(12) United States Patent  
Kaneto (10) Patent No.: US 8,338,993 B2  
(45) Date of Patent: Dec. 25, 2012

(54) ACTUATOR USING MAGNETIC FORCE, AND DRIVE DEVICE AND SENSOR USING THE SAME

(75) Inventor: Keiichi Kaneto, Kitakyushu (JP)

(73) Assignee: Kyushu Institute of Technology, Kitakyushi-shi (JP)

( * ) Notice: Subject to any disclaimer, the term of this patent is extended or adjusted under 35 U.S.C. 154(b) by 154 days.

(21) Appl. No.: 12/808,316

(22) PCT Filed: Dec. 8, 2008

(86) PCT No.: PCT/JP2008/072249  
§ 371 (c)(1),  
(2), (4) Date: Jun. 15, 2010

(87) PCT Pub. No.: WO2009/084378  
PCT Pub. Date: Jul. 9, 2009

(65) Prior Publication Data  
US 2010/0277011 A1  Nov. 4, 2010

(30) Foreign Application Priority Data  
Dec. 28, 2007 (JP) ................ 2007-340048

(51) Int. Cl.  
*H02N 2/00* (2006.01)  
*H01F 1/00* (2006.01)  
*H01F 3/00* (2006.01)

(52) U.S. Cl. ............ 310/26; 335/296; 335/303

(58) Field of Classification Search .......... 310/300, 310/309, 311, 365, 800, 15–39; 335/296, 335/303; *H02N 1/00, 2/00, 11/00*  
See application file for complete search history.

(56) References Cited

U.S. PATENT DOCUMENTS 2,532,876 A * 12/1950 Asche et al. .......... 335/230  
4,176,411 A * 12/1979 Runge ............... 623/3.11  
5,087,804 A  2/1992 McGaffigan  
(Continued)

FOREIGN PATENT DOCUMENTS

JP  59-144474  8/1984  
(Continued)

OTHER PUBLICATIONS

International Search Report for International Application No. PCT/JP2008/072249 dated Feb. 26, 2009.  
(Continued)

*Primary Examiner* — Quyen Leung  
*Assistant Examiner* — Thomas Truong  
(74) *Attorney, Agent, or Firm* — Kratz, Quintos & Hanson, LLP (57) ABSTRACT

To provide an actuator that can flexibly and softly move like muscles, can maintain a stable operation over a long period of time, can generate a strong driving force, has a rapid input response, has a favorable sensitivity, has a high energy conversion efficiency, and can be accurately controlled, a coil is embedded in a magnetic elastomer obtained by mixing a powder-like ferromagnetic or highly magnetic permeable material with an elastomer, so that the coil can be electrically connected. By electrically connecting the coil, a magnetic field generates in the coil and around the coil. The magnetic field penetrates the magnetic elastomer. When the magnetic field generates in the magnetic elastomer, deformation force acts on the magnetic elastomer by the magnetic force acting on each portion in the magnetic elastomer. Thus, driving force can be obtained.

3 Claims, 8 Drawing Sheets

U.S. PATENT DOCUMENTS

| | | | |
|---|---|---|---|
| 5,090,248 A * | 2/1992 | Cimmino et al. | 73/780 |
| 5,977,685 A * | 11/1999 | Kurita et al. | 310/311 |
| 6,781,284 B1 * | 8/2004 | Pelrine et al. | 310/330 |
| 7,191,963 B2 * | 3/2007 | Cobianchi et al. | 239/585.1 |
| 7,518,284 B2 * | 4/2009 | Benslimane et al. | 310/311 |
| 8,076,931 B2 * | 12/2011 | Lenglet | 324/253 |
| 2004/0217671 A1 | 11/2004 | Rosenthal | |
| 2006/0050189 A1 | 3/2006 | Ito | |
| 2007/0241849 A1 * | 10/2007 | Heinrich et al. | 335/215 |
| 2008/0217926 A1 * | 9/2008 | Lemieux | 290/1 R |
| 2008/0252289 A1 * | 10/2008 | Lenglet | 324/253 |

FOREIGN PATENT DOCUMENTS

| | | |
|---|---|---|
| JP | 3-293980 | 12/1991 |
| JP | 6-6991 | 1/1994 |
| JP | 11-169393 | 6/1999 |
| JP | 11-169394 | 6/1999 |
| JP | 2004-188523 A1 | 7/2004 |
| JP | 2006-299842 A1 | 11/2006 |
| JP | 2007-138721 A1 | 6/2007 |
| JP | 2007-247593 A1 | 9/2007 |
| JP | 2007-267471 A1 | 10/2007 |
| JP | 2007-318960 A1 | 12/2007 |
| WO | WO 92/12609 A1 | 7/1992 |
| WO | WO 2004/079832 A2 | 9/2004 |
| WO | WO 2007042646 A1 * | 4/2007 |

OTHER PUBLICATIONS

Japan Office Action dated Aug. 8, 2012 issued for the corresponding Japanese patent application No. JP2007-340048 with English translation.

* cited by examiner

(a) stretching
(swelling and contraction)

(b) flexion (c) twisting

ACTUATOR USING MAGNETIC FORCE, AND DRIVE DEVICE AND SENSOR USING THE SAME

TECHNICAL FIELD

The present invention relates to an actuator using magnetic force capable of flexibly performing exercises, such as stretching, flexion, or twisting, a drive device using the same, and a sensor using the same structure as that of the actuator.

BACKGROUND ART

Drive devices typified by robots mostly use a motor. However, general motors are heavy and have problems of occurrence of sounds, vibration, and electric noises. Thus, in fields of robots with high human compatibility, such as welfare robots and robots for rehabilitation, a demand for soft actuators that softly and strongly move like muscles instead of motors has being increased.

As former soft actuators, an IPMC actuator using an ionic conductive polymer (IPMC: Ionic Polymer Metal Composite), an SMA actuator using a shape memory alloy (SMA), a soft actuator utilizing electrochemical stretching of a conductive polymer, and the like have been developed.

In the IPMC actuator, when a voltage is applied to the ionic polymer metal composite containing an electrolyte, positive ions move to the negative pole side and, simultaneously therewith, a large amount of water having positive ions moves to the negative pole side in the polymer. As a result, the polymer swells at the negative pole side in which water has gathered with the positive ions. In contrast, at the positive pole side, the polymer contracts corresponding to the amount in which water has decreased. The polymer bends due to the phenomenon of swelling and contraction, which is used as the power for the actuator.

The IPMC actuator has advantages in that driving with a relatively low driving voltage (about 1.5 V) can be achieved, the responsiveness is high (0.1 second or lower), the durability is high (allowing 100,000 or more times of bending), the size can be easily reduced, the power consumption is low, and driving over a long period of time can be achieved. Thus, a large amount of research and development has been performed for the IPMC actuator at present (e.g., Patent Documents 1 to 3).

The SMA actuator utilizes, as an actuator, a phenomenon in which even when a shape memory alloy, in which a given shape is memorized beforehand, is deformed by applying a stress at a low temperature, the alloy recovers the shape memorized beforehand upon heating the same at a temperature higher than a certain temperature (e.g., Patent Documents 4 and 5). The SMA actuator has advantages in that the generative force is high and the structure of a high shrinkage structure is easy.

In the soft actuator utilizing electrochemical stretching of the conductive polymer, the chemical structure of the polymer or polymer structure changes due to an electrical oxidation-reduction reaction by applying electricity to the conductive polymer, whereby motions like muscles are developed in the polymer (Patent Documents 6 to 8). The soft actuator of this type has advantages in that the shape is easily maintained, the power conversion efficiency is high, driving with a voltage as low as 1.5 V or lower can be achieved, the size can be easily reduced, and the weight is light.

[Patent Document 1]
Japanese Unexamined Patent Application Publication No. 6-6991

[Patent Document 2]
Japanese Unexamined Patent Application Publication No. 2007-267471

[Patent Document 3]
Japanese Unexamined Patent Application Publication No. 2007-318960

[Patent Document 4]
Japanese Unexamined Patent Application Publication No. 2007-247593

[Patent Document 5]
Japanese Unexamined Patent Application Publication No. 2007-138721

[Patent Document 6]
Japanese Unexamined Patent Application Publication No. 11-169393

[Patent Document 7]
Japanese Unexamined Patent Application Publication No. 11-169394

[Patent Document 8]
Japanese Unexamined Patent Application Publication No. 2006-299842

DISCLOSURE OF INVENTION

Problems to be Solved by the Invention

However, since the IPMC actuator utilizes an electrolyte, there is a problem in that when the IPMC actuator is used over a long period of time, the electrolyte deteriorates and is likely to become unstable. Moreover, since the swelling and contraction of the polymer are utilized as driving force, the IPMC actuator also has problems in that the driving force is relatively low, accurate control is difficult, rapid stopping during driving is difficult, and the actuator cannot be used under a dry environment.

Since the SMA actuator utilizes thermal changes, such as heating or cooling, in the shape memory alloy, there is a problem in that the responsiveness of the shape memory alloy particularly during cooling is low. Moreover, since heat diffusion also occurs, the SMA actuator has a problem in that the energy efficiency is low.

The soft actuator utilizing the electrochemical stretching of the conductive polymer has a high generative force compared with the IPMC actuator. However, since an electrolyte is utilized, there is a problem in that when used over a long period of time, the electrolyte deteriorates and is likely to become unstable. Since the soft actuator also utilizes structural changes in the polymer, the soft actuator has disadvantages in that the response rate is low and the energy conversion efficiency is also low.

Thus, it is an object of the present invention to provide an actuator that can maintain stable operation over a long period of time, can generate a strong driving force, has a rapid input response, has a favorable sensitivity, has a high energy conversion efficiency, and can be accurately controlled while maintaining the properties of the former soft actuators, e.g., flexibly, softly, and strongly moving like muscles, and a drive device using the same.

It is another object of the present invention to provide a sensor having the same structure as that of the actuator of the present invention and can detect deformation due to external force.

Means for Solving the Problems

According to a first structure of an actuator of the present invention, a coil is embedded in a magnetic elastomer obtained by mixing a ferromagnetic material with an elastomer, so that the coil can be electrically connected.

According to the structure, by electrically connecting to the coil, a magnetic field generates in the coil or around the coil. Since the coil is embedded in the magnetic elastomer, the magnetic field penetrates the magnetic elastomer. When the magnetic field generates in the magnetic elastomer, deformation force acts on the magnetic elastomer due to magnetic force acting on each portion in the magnetic elastomer. Thus, driving force can be obtained.

Since the coil is completely embedded in the magnetic elastomer, all the generated magnetic fluxes penetrate the magnetic elastomer. Thus, the energy conversion efficiency is very high and a strong driving force can be generated. Due to the elasticity of the magnetic elastomer, the actuator flexibly and softly moves like muscles. Furthermore, unlike the former soft actuator described above, an electrolyte is not used and a chemical reaction or molecular structure changes do not occur associated with the operation. Thus, stable operation can be maintained over a long period of time. In principle, since magnetism generated in the coil by electrical connection is used similarly as in the former motor, the input response is high and the sensitivity is favorable similarly as in usual motors. By controlling a current to be applied to the coil, accurate control can be achieved.

Here, the "ferromagnetic material" refers to a material in which adjacent spins are aligned in the same direction and which has a large magnetic moment as a whole and refers to a material that can obtain spontaneous magnetization even when there are no external magnetic fields. As the "ferromagnetic material", inorganic ferromagnetic materials, such as iron, ferrite, OP, MnBi, barium ferrite, Supermalloy, Al—Ni—Co, samarium-cobalt, neodymium iron boron, and samarium iron nitrogen, or organic ferromagnetic materials can be used, for example. When the ferromagnetic materials are mixed with an elastomer, they can be mixed in the form of powder, liquid, or colloid. The "elastomer" refers to a substance that is constituted by polymerized substances, such as rubber, plastic, or resin and that has elasticity with which the substance, which is extended with a low stress, recovers the original length immediately after the stress is relieved. As the "elastomer", crude rubber, synthetic rubber, butyl rubber, and the like can be used, for example.

According to a second structure of an actuator of the present invention, a coil is embedded in a magnetic elastomer obtained by mixing a highly magnetic permeable material with an elastomer, so that the coil can be electrically connected.

Also according to the structure, the driving force of the actuator can be obtained due to the same action as that of the first structure.

Here, the "highly magnetic permeable material" refers to a material having a high relative permeability. It is preferable to use materials having a relative permeability of preferably 10 or more. When the relative permeability is higher, the driving force of the actuator when the coil is electrically connected becomes larger. In order to obtain a practically sufficient driving force, the relative permeability may be 10 or more. As the "highly magnetic permeable material", inorganic highly magnetic permeable materials, such as iron, ferrite, soft ferrite, OP, MnBi, barium ferrite, Permalloy, Supermalloy, silicon steel, Sendust, permendur, an amorphous magnetic alloy, and a nanocrystal magnetic alloy, or organic highly magnetic permeable materials can be used. Also in this case, when the highly magnetic permeable materials are mixed with an elastomer, they can be mixed in the form of powder, liquid, or colloid. In actual, the appropriate value of the relative permeability of the highly magnetic permeable materials is determined by a ratio with the Young's modulus of the elastomer as described later. When the relative permeability of the highly magnetic permeable material is defined as $\mu_r$ and the Young's modulus of the elastomer is defined as Y[Pa], it is preferable to satisfy $\mu_r/Y > 1$ [Pa$^{-1}$] in order to obtain an actuator that is resistant against frequent practical use.

According to a third structure of an actuator of the present invention, the coil is a spiral coil in which a lead is spirally wound in the first or the second structure.

According to the structure, the actuator can generate a stretching movement.

According to a fourth structure of an actuator of the present invention, the coil is a zigzag coil in which a lead is repeatedly bent in a zigzag manner in the first or the second structure.

According to the structure, the actuator can generate a stretching movement.

Here, the "zigzag coil" refers to a coil having a shape in which a lead is repeatedly bent in a zigzag manner and refers to a coil having the same shape as that of the "zigzag spring" specified in JIS B 0103.

According to a fifth structure of an actuator of the present invention, the spiral coil in which the lead is spirally wound and the zigzag coil in which the lead is repeatedly bent in a zigzag manner are embedded in parallel to each other in the magnetic elastomer in the first or the second structure.

According to the structure, the actuator can generate a stretching movement.

According to a sixth structure of an actuator of the present invention, a plurality of the coils that can be independently electrically connected are embedded in series in the magnetic elastomer in the first or the second structure.

According to the structure, the actuator can generate an alternately stretching movement.

According to a seventh structure of an actuator of the present invention, a first torus coil and a second torus coil that are formed by bending the spiral coil, in which the lead is spirally wound, into an annular shape are provided and the first torus coil and the second torus coil are embedded in the magnetic elastomer in a state where the central axes are orthogonal to each other in the first or the second structure.

According to the structure, the actuator can generate a twisting movement.

According to a first structure of a drive device of the present invention, the actuator having any one of the first to seventh structures or a plurality of the actuators is/are used as the source of power.

According to a first structure of a sensor of the present invention, a detector in which a coil is embedded and a detection member for detecting a voltage or a current generating in the coil are provided in a magnetic elastomer obtained by mixing a ferromagnetic material with an elastomer.

According to the structure, the deformation of the detector can be detected.

According to a second structure of a sensor of the present invention, a detector in which a coil is embedded and a detection member detecting a voltage or a current generating in the coil are provided in a magnetic elastomer obtained by mixing a highly magnetic permeable material with an elastomer.

According to the structure, the deformation of the detector can be detected.

Effects of the Invention

As described above, according to the actuator of the invention, by structuring so that a coil is embedded in a magnetic elastomer, a magnetic field is formed in the magnetic elastomer by electrically connecting the coil, and the magnetic elastomer is deformed by the magnetic force generated by the magnetic field, the properties of the former soft actuator, e.g., flexibly, softly, and strongly moving like muscles, can be achieved. Moreover, since an electrolyte is not utilized and chemical changes do not arise when driving, stable operation over a long period of time can be achieved. Since a motor thereof is the same as that of a former magneto-type motor in driving by magnetic force acting on a magnetic substance, the responsiveness is high, the sensitivity is high, a strong driving force can be generated, and electrically accurate control can be performed. Furthermore, the coil is embedded in the magnetic elastomer, and all the generated magnetic fluxes in the coil penetrate the magnetic elastomer. Thus, a high energy conversion efficiency can be achieved.

REFERENCE NUMERALS 1, 1', 5, 6, 9 Actuator
2 Magnetic elastomer
3 Spiral coil
4 Zigzag coil
7 Drive device
8 Valve
10, 11 Torus coil
12 Detector
13 Detection member

BEST MODES FOR CARRYING OUT THE INVENTION

Figure 1:
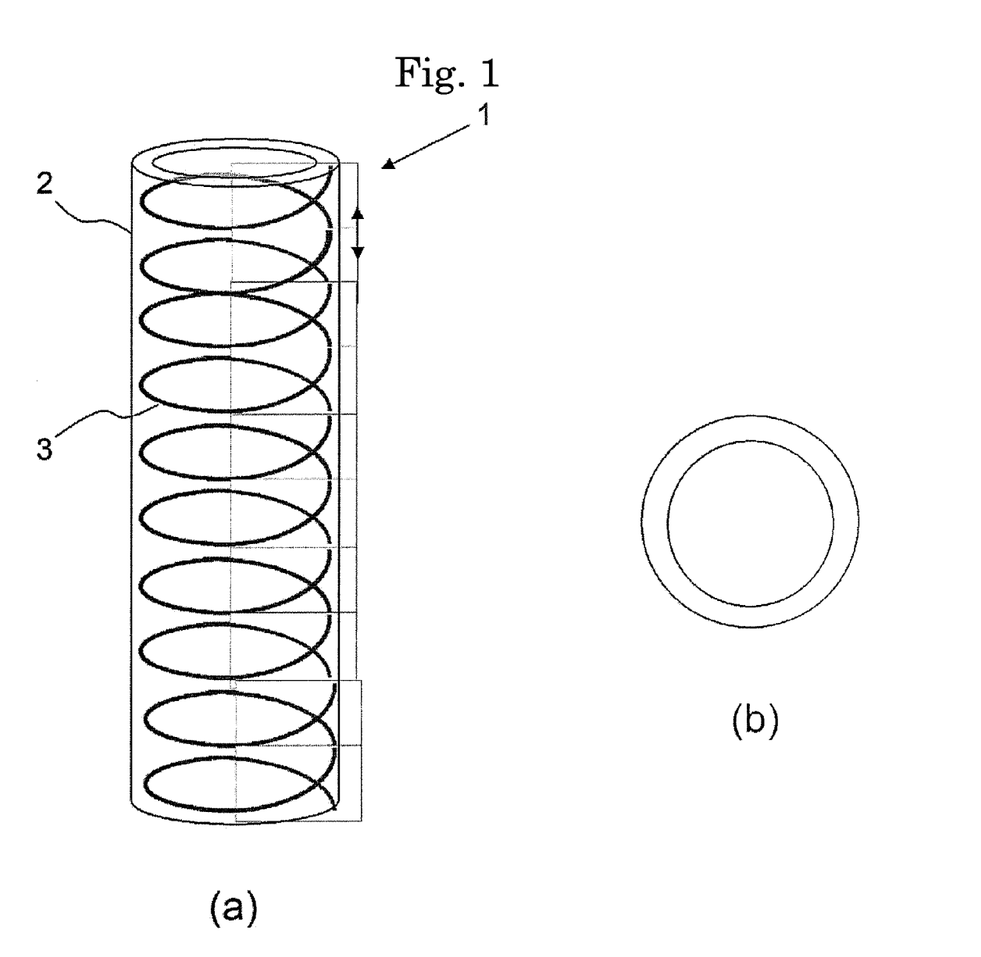
FIG. 1 is a view illustrating the structure of an actuator 1 according to Example 1 of the present invention.

Hereinafter, the best modes for carrying out the present invention will be described with reference to the drawings.
First Embodiment
FIG. 1 is a view illustrating the structure of an actuator 1 according to Example 1 of the present invention. In FIG. 1, the actuator 1 of this Example has a structure such that a spiral coil 3 in which a lead is spirally wound is embedded in a magnetic elastomer 2 formed into a cylindrical shape. The magnetic elastomer 2 is obtained by mixing a powder-like ferromagnetic or highly magnetic permeable material with an elastomer containing a synthetic rubber, a synthetic resin, plastic, and the like with a mixing roll or the like to prepare a magnetic elastomer, and then forming the magnetic elastomer. For the spiral coil 3, a general lead, such as copper or aluminum, is used. Both ends of the spiral coil 3 are drawn out to the outside (not shown), and the spiral coil 3 can be electrically connected from both the ends.

In this Example, in order to obtain a high coefficient of contraction and a high stretching force, the magnetic elastomer 2 is formed into a cylindrical shape having a hollow center, but, depending on the case, the shape of the magnetic elastomer 2 may be a columnar shape.

Figure 2:
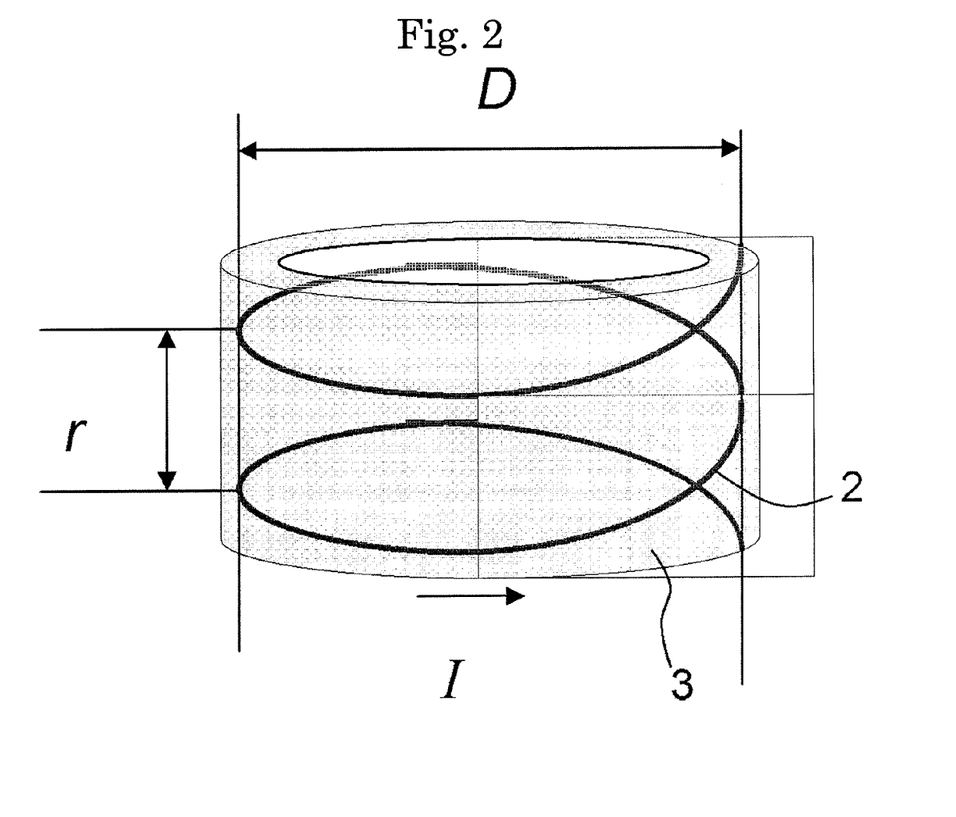
FIG. 2 illustrates a basic unit structure of the actuator 1 of FIG. 1.

As shown in FIG. 2, the diameter of the spiral coil 3 is defined as D and the spiral pitch thereof is defined as r. The relative permeability of the magnetic elastomer 2 is defined as $\mu_r$ and the vacuum magnetic permeability thereof is defined as $\mu_0$. When a current I is applied to the spiral coil 3, force $F_0$ acting on a 2-turn partial coil shown in FIG. 2 is represented by Formula (1). The force $F_0$ acts in the direction in which the coil contracts.

[Equation 1]

$$F_0 = \frac{\mu_r \mu_0 I^2 D}{2r} \quad (1)$$

When the number of turns of the spiral coil 3 is defined as n turns, contraction force F of the coil at both the ends of the spiral coil 3 is as represented by Formula (2).

[Equation 2]

$$F = \frac{\mu_r \mu_0 I^2 D}{2r} \beta_n \quad (2)$$

Here, $\beta_n$ is a correction for a multi-magnetic field between leads by winding the lead by n turns.

EXAMPLE 1

The relative permeability $\mu_r$ of the magnetic elastomer 2 is adjusted to be $10^5$, the coil diameter D of the spiral coil 3 is adjusted to be 5 mm, the pitch r thereof is adjusted to be 1 mm, and the number of turns thereof is adjusted to be 2. The coil length is 3 mm. A current to be applied to the spiral coil 3 is adjusted to 1 A. The contraction force generating in the spiral coil 3 in this case is as represented by the following formula.

[Equation 3]

$$F_0 = \frac{10^5 \times 1.26 \times 10^{-6} \times 1^2 \times 5 \times 10^{-3}}{2 \times 1 \times 10^{-3}} = 0.315[N] \quad (3)$$

The maximum weight that can be lifted by the force in a gravitational field is determined as follows. When the acceleration of gravity is defined as g=9.8 m/s², the initial contraction force is as represented by the following formula considering $F_0$=mg.

[Equation 4]

$$m = \frac{F_0}{g} = 32[\text{g weight}] \quad (4)$$

Thus, contraction force with which a 32 g weight is lifted arises. In this calculation, the elastic modulus of the magnetic elastomer 2 is not considered.

(End of Example 1)

Next, the degree of stretching of the actuator 1 will be examined. The degree of stretching is determined by the Young's modulus Y of the magnetic elastomer 2. When the Young's modulus is higher, the magnetic elastomer 2 becomes hard. When the magnetic elastomer 2 is softer, an actuator that contracts on a large scale is obtained.

The relationship between a stress f per unit area applied to the magnetic elastomer 2 and a deformation (degree of stretching) $\Delta l$ is as follows.

[Equation 5]

$$f = Y\Delta l$$

$$f = Y\Delta l \quad (5)$$

Thus, when the cross sectional area of the magnetic elastomer 2 is defined as $S_G$, the following formula (6) is established based on force equilibrium conditions.

[Equation 6]

$$F_0 = fS_G = S_G Y\Delta l \quad (6)$$

Thus, the degree of stretching relative to the 2-turn basic unit is as represented by Formula (7).

[Equation 7]

$$\Delta l = \frac{F_0}{S_G Y} = \frac{\mu_r \mu_0 I^2 D}{2rYS_G} \quad (7)$$

EXAMPLE 2

The outer diameter of the magnetic elastomer 2 is adjusted to 5.5 mm and the inner diameter thereof is adjusted to 4.5 mm. In this case, the cross sectional area of the magnetic elastomer 2 is $S_G = 7.85 \times 10^{-6}$ m². When the Young's modulus of a composite of the magnetic elastomer 2 and the spiral coil 3 is defined as $Y = 10^5$ Pa, $S_G Y = 0.785$N is established. Thus, according to Formula (3), $\mu I = 0.315/S_G Y = 0.40$ is established, and a degree of stretching of 40% can be achieved.

(End of Example 2)

In the evaluation above, the thickness of the spiral coil 3 is disregarded. Thus, in actual, when the thickness of the spiral coil 3 is considered, the coefficient of contraction as a whole becomes small corresponding to the considered thickness. When contracting, the distance (pitch) between the coils decreases, and thus the contraction force further increases.

According to Formula (7), the performance of the actuator 1 of this Example is favorable when the magnetic permeabilities $\mu_r$ and $\mu_0$ of the magnetic elastomer 2 are high and when the Young's modulus Y of the composite of the magnetic elastomer 2 and the spiral coil 3 is lower. As the standard values thereof, when the values are equal to or higher than those represented by the following formula,

[Equation 8]

$$\frac{\mu_r}{Y} = \frac{10^5}{10^5} > 1 [Pa^{-1}] \quad (8)$$

the actuator 1 that is resistant against frequent practical use can be produced.

Finally, the electrical properties of the actuator 1 will be described with reference to easy example.

EXAMPLE 3

For the wire of the spiral coil 3, a copper wire is used and the wire diameter t is adjusted to 0.3 mm. Since the wire rod is a copper wire, the electrical conductivity is represented by $\sigma = 59.6 \times 10^6$ S/m. When the copper wire is formed into a coil having a diameter D of 5 mm and the number of turns n is adjusted to 2, the cross sectional area s, length L, and resistance R of the wire rod are as represented by Formulae (9a) to (9c).

[Equation 9]

$$s = \pi(0.15 \times 10^{-3})[m^2] \quad (9a)$$

$$L = 2\pi D[m] \quad (9b)$$

$$R = \frac{L}{\sigma s} = \frac{2\pi \times 5 \times 10^{-3}}{59.6 \times 10^6 \times \pi \times (0.15 \times 10^{-3})^2} = 8 \times 10^{-3} \Omega \quad (9c)$$

Thus, a current of 1 A is applied, a Joule heat of 8 mW generates.

(End of Example 3)

(Second Embodiment)

Figure 3:
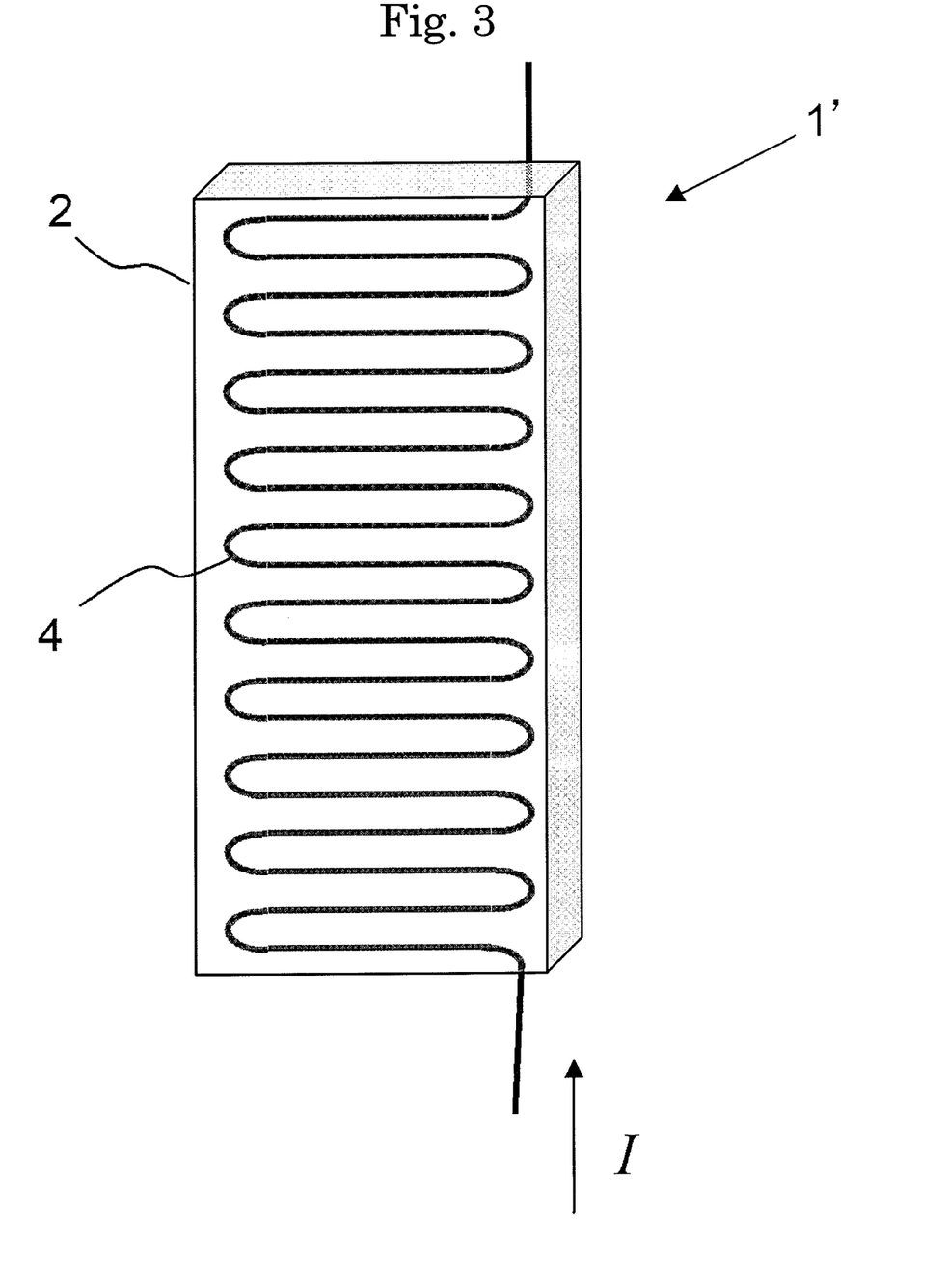
FIG. 3 is a view illustrating the structure of an actuator 1' according to Example 2 of the present invention.

FIG. 3 is a view illustrating the structure of an actuator 1' according to Example 2 of the present invention. The actuator 1' of this Example has a structure such that a zigzag coil 4 in which a lead is repeatedly bent in a zigzag manner is embedded in the magnetic elastomer 2 that is formed into a flat cube. The magnetic elastomer 2 is obtained, in the same manner as in Working Example 1, by mixing a powder-like ferromagnetic or highly magnetic permeable material with an elastomer containing a synthetic rubber, a synthetic resin, plastic, and the like with a mixing roll or the like to prepare a magnetic elastomer, and then forming the magnetic elastomer. For the zigzag coil 4, a usual lead, such as copper or aluminum, is used in the same manner as in Example 1. Both ends of the zigzag coil 4 are drawn out to the outside of the magnetic elastomer 2 and the zigzag coil 4 can be electrically connected from both the ends.

Figure 4:
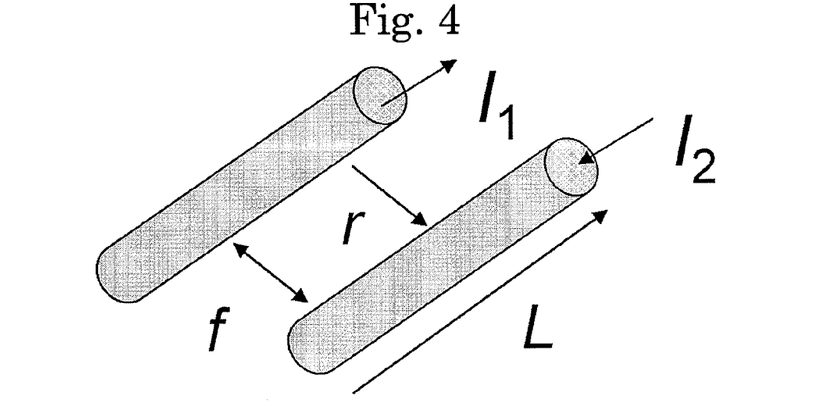
FIG. 4 is a basic unit structure of the actuator 1' of FIG. 3.

The principle of the operation of the actuator 1' is as follows. The leads parallel to each other of the zigzag coil 4 can be approximately modeled with two parallel leads as shown in FIG. 4. To the two parallel leads of FIG. 4, a current $I_1$ and a current $I_2$ are applied, respectively, in the directions opposite to each other. In this case, the force acting between the two leads is represented by formula (10). Here, the minus mark represents that repulsive force acts between the two leads.

[Equation 10]

$$f = -\frac{\mu_r \mu_0 I_1 I_2 L}{2\pi r} \quad (10)$$

Here, $\mu_r$ is the relative permeability of the magnetic elastomer 2, $\mu_0$ is the vacuum magnetic permeability thereof, L is the length of each lead, and r is the distance between the two leads.

Thus, it is found that the actuator 1' elongates by applying a current to the zigzag coil 4 of the actuator 1' of FIG. 3.

Third Embodiment

Figure 5:
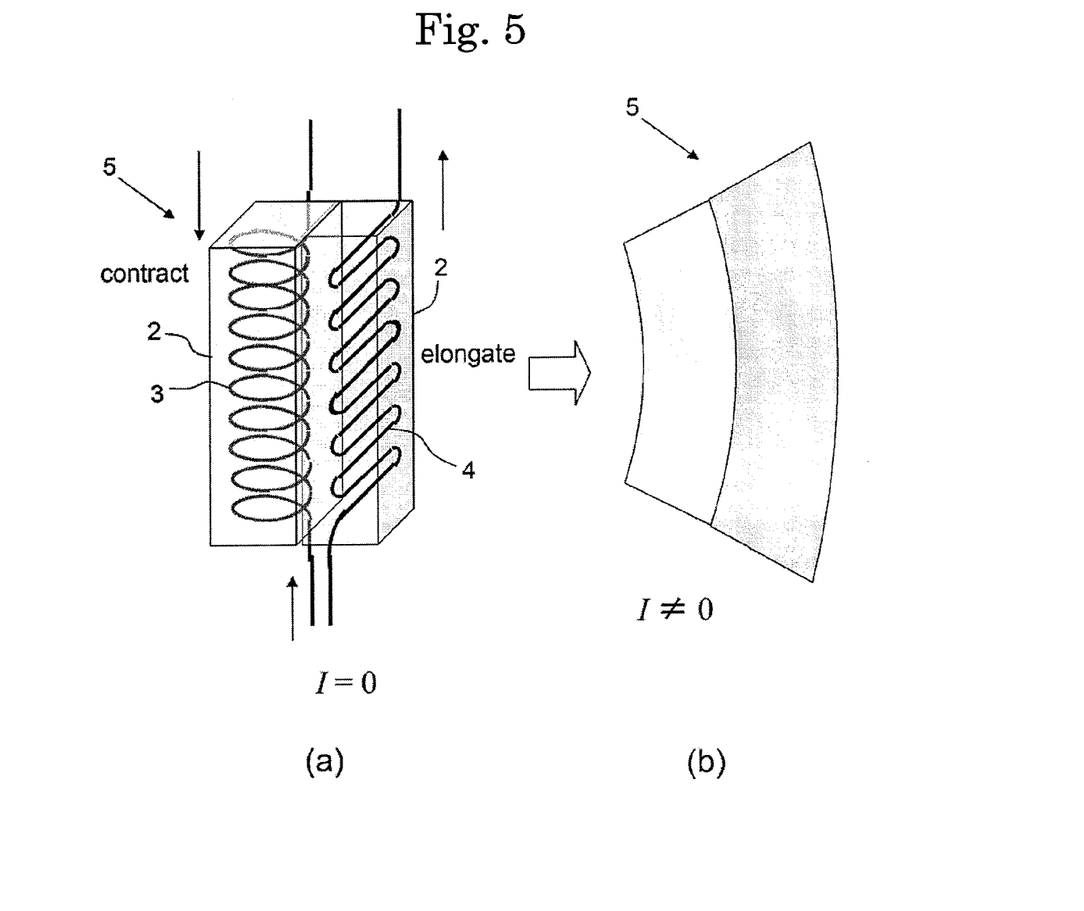
FIG. 5 is a view illustrating the structure of an actuator 5 according to Example 3 of the present invention.

FIG. 5 is a view illustrating the structure of an actuator 5 according to Example 3 of the present invention. FIG. 5(a) illustrates a state in which the actuator 5 is not electrically connected and FIG. 5(b) illustrates a state in which the actuator 5 is electrically connected. In the actuator 5, the spiral coil 3 in which a lead is spirally wound and the zigzag coil 4 in which a lead is repeatedly bent in a zigzag manner are embedded in parallel to each other in the magnetic elastomer 2. In FIG. 5, the magnetic elastomer 2 is divided into two portions of a right portion and a left portion for description, but, in actual, the magnetic elastomer 2 is integrally formed.

Figure 6:
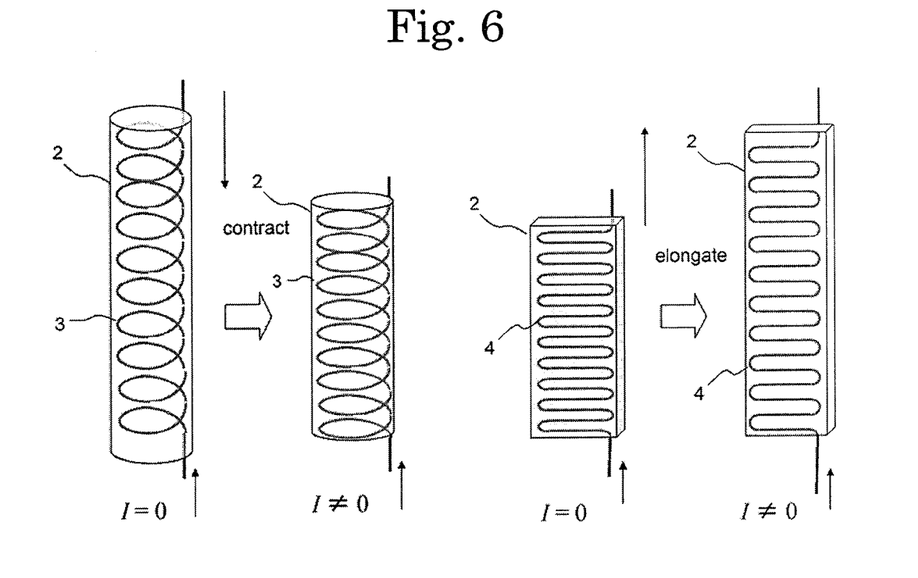
FIG. 6 is a view illustrating the operation of each of the actuator 1 and actuator 1'.

The spiral coil 3 is the same as that of Example 1 and the zigzag coil 4 is the same as that of Example 2. When a current is applied to the spiral coil 3, the spiral coil 3 contracts as described in Example 1. In contrast, when a current is applied to the zigzag coil 4, the zigzag coil 4 elongates as described in Example 2 (FIG. 6). Thus, when a current is applied to the spiral coil 3 and the zigzag coil 4 of the actuator 5 of FIG. 5, the left side in which the spiral coil 3 is embedded contracts and the right side in which the zigzag coil 4 is embedded elongates. As a result, a flexion movement as shown in FIG. 5(b) occurs.

Fourth Embodiment

Figure 7:
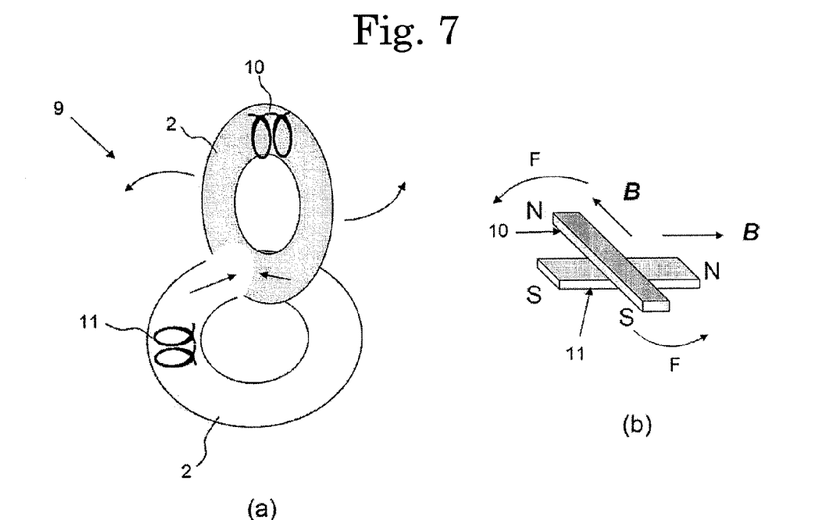
FIG. 7 is a view illustrating the structure of an actuator 9 according to Example 4 of the present invention.

FIG. 7 is a view illustrating the structure of an actuator 9 according to Example 4 of the present invention. FIG. 7(a) illustrates the structure of the actuator 9 and FIG. 7(b) illustrates the principle of the operation of the actuator 9.

The actuator 9 has two torus coils 10 and 11 that are formed by bending the spiral coil, in which a lead is spirally wound, into an annular shape. The respective torus coils 10 and 11 are embedded in the magnetic elastomer 2 formed into a torus shape. The torus coil 10 and the torus coil 11 are disposed so that the central axes are orthogonal to each other.

When a current is applied to the torus coils 10 and 11, the torus coils 10 and 11 become two electromagnets that are orthogonal to each other as shown in FIG. 7(b). Thus, twisting force indicated by the arrow F shown in FIG. 7 (b) acts between the torus coils 10 and 11 due to the interaction of these two electromagnets. More specifically, the actuator 9 can generate a twisting movement.

Figure 8:
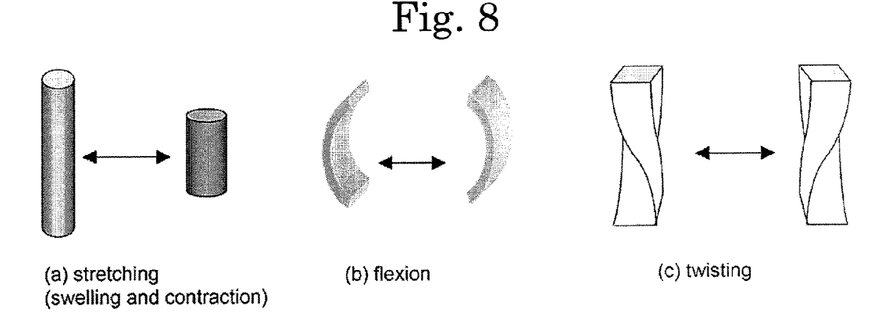
FIG. 8 is a view illustrating the operation of the actuators of Examples 1, 3, and 4.

FIG. 8 is a view illustrating the operation of the actuators of Examples 1, 3, and 4. The actuator 1 of Example 1 generates a stretching movement as shown in FIG. 8(a). The actuator 5 of Example 3 generates a flexion movement as shown in FIG. 8(b). The actuator 9 of Example 4 generates a twisting movement as shown in FIG. 8(c). Thus, the use of the three kinds of the actuators 1, 5, and 9 allows generation of all the movements required in soft actuators. For example, when the actuator for a stretching movement or a flexion movement of muscles is used for joints, such as the knee, elbow, and finger, the actuator for a flexion movement and a twisting movement is used for the hip joint and shoulder, and the actuator for a stretching movement is used for the skeletal muscles and internal organs, such as the heart and stomach, the movements can be reproduced.

Fifth Embodiment

Figure 9:
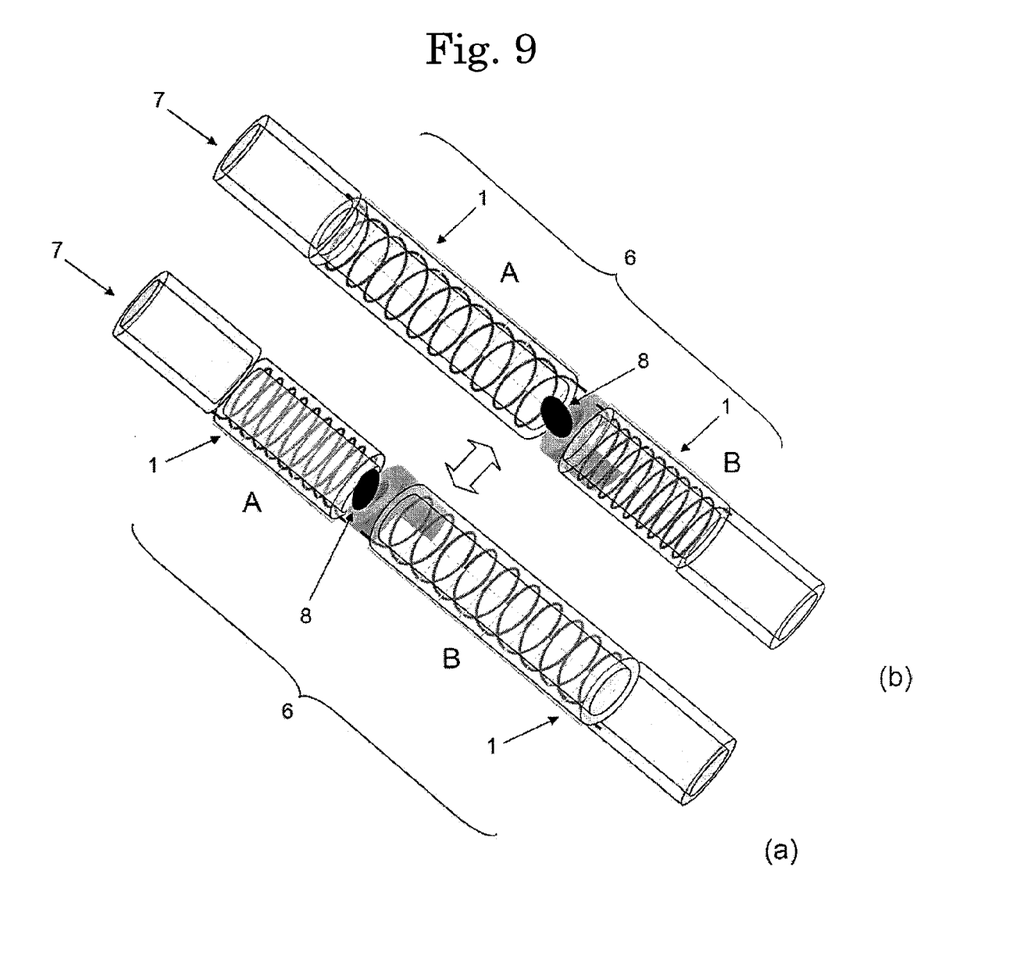
FIG. 9 is a view illustrating the structure of a drive device 7 using the actuator 6 according to Example 5 of the present invention.

FIG. 9 is a view illustrating the structure of a drive device 7 using an actuator 6 according to Example 5 of the present invention. The actuator 6 has a structure such that two pieces of the actuator 1 of Example 1 are disposed in series. The two actuators 1 can be independently electrically connected. The drive device 7 having the actuator 6 has a structure such that a valve 8 is interposed between the two actuators 1,1 and the two actuators 1, 1 are connected in the shape of a straight tube.

By alternately applying a current to the actuators 1, 1, a linear pump can be structured in which one of the actuators elongates and the other one thereof contracts (FIG. 9). In FIG. 9(a), the left actuator 1(A) is electrically connected and the right actuator 1(B) is not electrically connected. In this case, the actuator 1(A) contracts and the actuator 1(B) elongates. In FIG. 9(b), the left actuator 1(A) is not electrically connected and the right actuator 1(B) is electrically connected. In this case, the actuator 1(B) contracts and the actuator 1(A) elongates. Thus, by alternately applying a current to the actuators 1(A) and 1(B), the drive device 7 functions as a linear pump.

Sixth Embodiment

Figure 10:
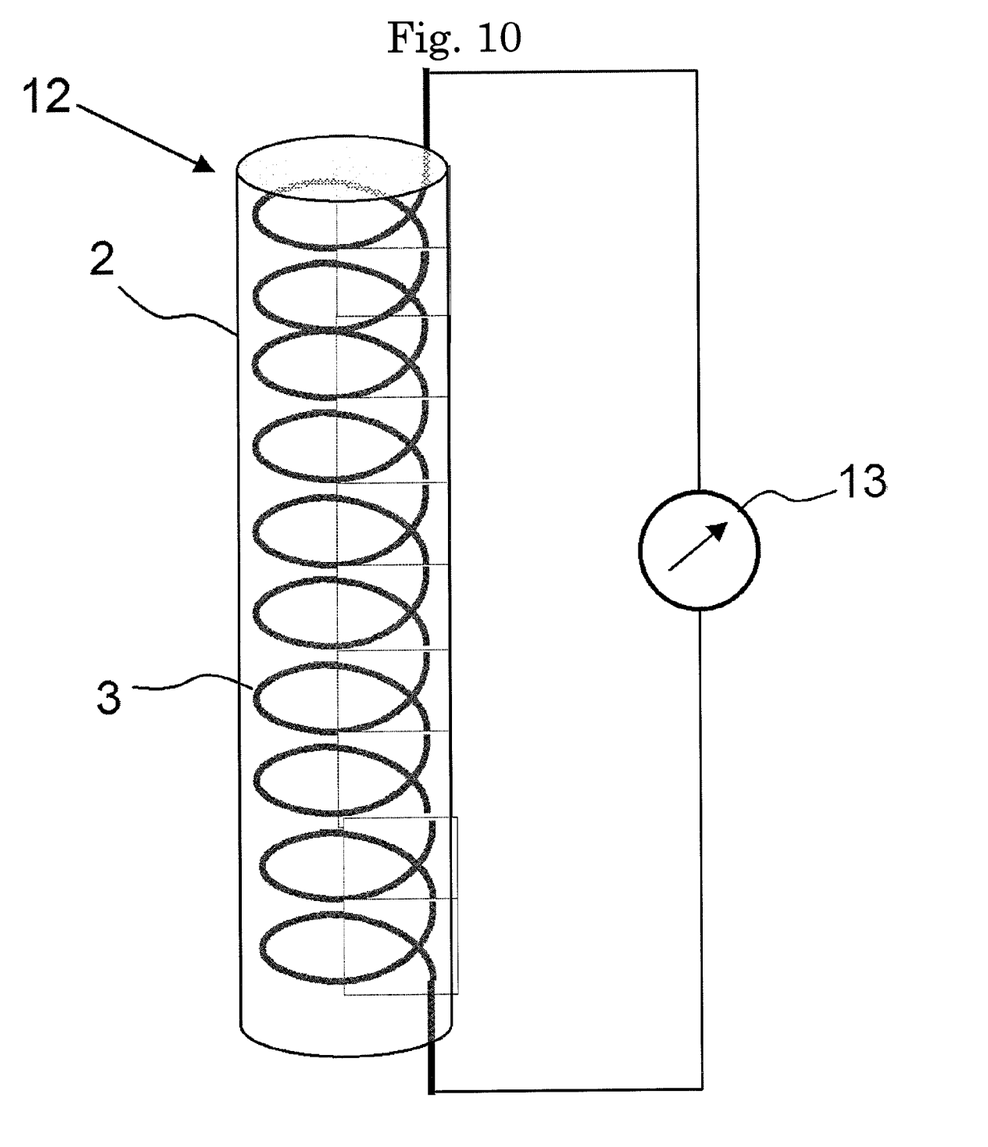
FIG. 10 is a view illustrating the structure of a sensor according to Example 6 of the present invention.

FIG. 10 is a view illustrating the structure of sensor according to Example 6 of the present invention. In FIG. 10, the magnetic elastomer 2 and the spiral coil 3 constituting a detector 12 are the same as those of FIG. 1. The magnetic elastomer 2 is constituted by mixing a powder-like ferromagnetic or highly magnetic permeable material with an elastomer. To both ends of the spiral coil 3 of the detector 12, a detection member 13 for detecting a current generating in the spiral coil 3 is connected.

With this structure, when compressing force or elongating force is applied to the detector 12 and thus the detector 12 is compressed and deformed or elongated and deformed, a magnetic field passing the spiral coil 3 changes. Thus, electromotive force generates in the spiral coil 3 due to electromagnetic induction, and a current is applied. By detecting the current by the detection member 13, the deformation degree of the detector 12 can be detected.

In order to achieve favorable detection sensitivity, it is preferable to use a material with which a ferromagnetic material has been mixed as materials of the magnetic elastomer 2. It is more preferable to use an anisotropic magnetic-elastomer in which the magnetization of the ferromagnetic material is oriented in one direction as the magnetic elastomer 2. This is because a larger number of magnetic fluxes passing the spiral coil 3 can be generated.

In this Example, a detector having the same structure as that of the actuator 1 of FIG. 1 is used as the detector 12. However, it is a matter of course that detectors having the same structures as those of the actuator 1' of FIG. 3, the actuator 5 of FIG. 5, and the actuator 9 of FIG. 7 can also be used. Also in this case, it is preferable to use a magnetic elastomer in which a powder-like ferromagnetic or highly magnetic permeable material has been mixed with an elastomer as the magnetic elastomer 2.

The invention claimed is:

1. An actuator/sensor device comprising:
    a magnetic elastomer obtained by mixing a ferromagnetic material or a highly magnetic permeable material with an elastomer;
    a coil, further comprisina a continuous wire embedded within the magnetic elastomer in a configuration wherein adiacent portions of the wire are substantially parallel to one another, whereby generated magnetic flux penetrates the magnetic elastomer, and
    electrical connections to ends of the coil:
    wherein the coil further comprises
    a first torus coil and a second torus coil that are formed by bending a spiral coil, in which the lead is spirally wound, into a respective annular shape, wherein
    the first torus coil and the second torus coil are embedded in the magnetic elastomer in a state where central axes of the annular shapes are orthogonal to each other.

2. An actuator, comprising:
    a magnetic elastomer obtained by mixing a ferromagnetic material with an elastomer, and a coil, the coil being embedded in the magnetic elastomer, so that the coil can be electrically connected; wherein the coil further comprises a first torus coil and a second torus coil that are formed by bending a spiral coil, in which the lead is spirally wound, into an annular shape, wherein the first torus coil and the second torus coil are embedded in the magnetic elastomer in a state where the central axes are orthogonal to each other.

3. An actuator, comprising:

a magnetic elastomer obtained by mixing a highly magnetic permeable material with an elastomer, and a coil, the coil being embedded in the magnetic elastomer, so that the coil can be electrically connected; wherein the coil further comprises a first torus coil and a second torus coil that are formed by bending a spiral coil, in which the lead is spirally wound, into an annular shape, wherein the first torus coil and the second torus coil are embedded in the magnetic elastomer in a state where the central axes are orthogonal to each other.

* * * * *